(12) United States Patent
Labský et al.

(10) Patent No.: US 6,610,284 B1
(45) Date of Patent: Aug. 26, 2003

(54) PREPARATION FOR PREVENTION AND HEALING OF INFLAMMATION AFFECTIONS

(75) Inventors: Jiří Labský, Praha (CZ); Jiří Vacík, Praha (CZ); Pavel Hošek, Karlovy Vary (CZ)

(73) Assignee: Institute of MacroMolecular Chemistry, Prague (CZ)

( * ) Notice: Subject to any disclaimer, the term of this patent is extended or adjusted under 35 U.S.C. 154(b) by 0 days.

(21) Appl. No.: 09/555,626

(22) PCT Filed: Oct. 2, 1998

(86) PCT No.: PCT/CZ98/00046

§ 371 (c)(1), (2), (4) Date: Jul. 27, 2000

(87) PCT Pub. No.: WO99/28359

PCT Pub. Date: Jun. 10, 1999

(30) Foreign Application Priority Data

Dec. 3, 1997 (CZ) ............................................... 3867-97

(51) Int. Cl.[7] ...................... A61K 31/74; A61K 31/785
(52) U.S. Cl. ................................ 424/78.26; 424/78.05; 424/78.08; 424/78.14
(58) Field of Search ................................ 424/78.26, 47, 424/61, 70.1, 70.17, 70.22, 78.05, 78.08, 78.14, DIG. 1

(56) References Cited

U.S. PATENT DOCUMENTS 4,719,099 A * 1/1988 Grollier et al. ............... 424/47

* cited by examiner

Primary Examiner—James M. Spear
Assistant Examiner—Blessing Fubara
(74) Attorney, Agent, or Firm—Notaro & Michalos P.C.

(57) ABSTRACT

A preparation for prevention and healing of inflammation affections comprising in an amount of 0.1 to 99.9% by weight derivatives of sterically hindered amines selected from the group consisting of: soluble polymers or copolymers prepared by radical polymerization in the presence of 0.01 to 10% by weight, of initiators prepared:in a polymerization mixture comprising individually or in combination an aliphatic amine monomer of the general formula (A), soluble polymers or copolymers prepared by radical polymerization in the presence of 0.01 to 10% by weight of initiators from monomers of cyclic sterically hindered amines of the general formula (B), soluble polymers prepared by polycondensation of difunctional sterically hindered amines of the general formula (F), soluble polymers or copolymers prepared by polycondensation of difunctional cyclic sterically hindered amines of the general formula (G), soluble copolymers prepared by polycondensation of difunctional cyclic, sterically hindered amines of the general formula (G) and monofunctional cyclic sterically hindered amines in an amount of 0.1 to 15%. by weight, based on the total polymerization mixture, of the general formula (H), derivatives of sterically hindered cyclic amines of the general formula (O), polymers, copolymers, or natural compounds comprising free reactive groups —OH, —$NH_2$, —COOH, —CHO, oxiranyl, selected from the group poly (vinyl alcohol), cellulose, (2-hydroxyethyl)cellulose, (carboxymethyl)cellulose, agar derivatives, polymers obtained by condensation, using alkanediol derivatives, oligomers and polymers of ethylene glycol or propylene glycol, natural or synthetic polymers, comprising a free carboxyl group, amino group or aldehyde group, prepared by additional functionalization of polymers or natural compounds by polymeranalogous reaction with a suitable sterically hindered amine.

3 Claims, 1 Drawing Sheet

PREPARATION FOR PREVENTION AND HEALING OF INFLAMMATION AFFECTIONS

This application is a 371 of PCT/CZ98/00046 filed Oct. 2, 1998.

TECHNICAL FIELD

The invention relates to a preparation for prevention and healing of inflammation affections having a radical scavenging capacity with a large biological spectrum coverage. The preparation is applicable to the prevention and healing of skin, hide, fascia and muscle surface injuries and wounds extending in various depths which are accompanied by a massive proliferation of radicals due to the oxygen reduction and by generation of reactive oxygen products.

BACKGROUND ART

Due to the effect of various types of radiation such as UV, gamma, X-ray and similar radiation as well as hyperoxia, xenobiotic, upon injury or as a result of certain diseases, the living organisms, may suffer from surface lesion affecting the skin, fascia, and muscle in different depth. Upon-any injury a massive proliferation of radicals occurs due to the oxygen reduction accompanied by generation of reactive oxygen compounds. The reason for the radical proliferation is a defect in coordination of redox enzymatic systems of the living tissue under injury as well as the activity of the leukocytes present. The reactive oxygen compounds, mostly of radical nature, have aggressive impact on biological systems and produce often irreparable changes, for example in reaction with lipids, proteins, or DNA and cause damage to physiological protective mechanisms preventing the biological systems from the adverse effect of reactive oxygen products. Simultaneously, enzymatic systems are activated, Which contributes to the generation of the reactive oxygen products.

The protective systems present physiologically in the living organisms are low-molecular weight compounds such as vitamins C, E, glutathione or macromolecular compounds such as enzymes, catalase, superoxide dismutase, glutathione, reductase, peroxidase or cyclooxygenases. In the event of a deep tissue damage the aforesaid compounds align with the phagocyte activity of leukocytes are not able to control the proliferation of free radicals to the extent which could ensure a satisfactory healing effect.

If a wound is attacked by bacteria, the reactive oxygen radicals may cause damage to the tissue but, on the other hand, they are not enough to stop the bacteria growth, which results in the degradation of the tissue macromolecules and in the accompanying penetration of leukocytes, which is the major reason for a pyogenic process. Subsequently, even if the production of bacterial flora is controlled, such radicals cause an excessive cytokine production, which promotes the growth of fibroblasts and, due to copious granulation, the epithelization is going down, which again results in a delayed healing process.

The conventional medical treatment mostly concentrates on the inflammation stage (using bacteria eliminating antibiotics, granulation medicaments, including prostaglandins) and is mostly insufficient in the epithelization stage, for example, a treatment of the wound may occur, however, granulations are poor or granulations are copious but the wound fails to come to epithelization.

SUMMARY OF INVENTION

The object of the invention of a preparation for prevention and healing of inflammation affections is to eliminate, to a considerable extent, the above inconvenience. The preparation comprises 0.1 to 99.9% by weight, derivatives of sterically hindered amines selected from the group consisting of:

soluble polymers or copolymers prepared by radical polymerization in the presence of 0.01 to 10% by weight of initiators in polymerization mixture comprising individually or in combination an aliphatic amine monomer of the general formula (A):

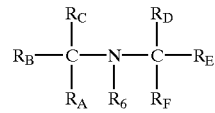

where $R_A$ to $R_F$ are: alkyl $C_1$–$C_4$, —$(CH_2)_n$— and n=3, 4, 5, polymerizable vinyl group in various combination and representation, $R_6$ is alkyl $C_1$–$C_4$, individually or in any combination, H, OH or oxygen radical obtained by additional oxidation; soluble polymers or copolymers prepared by radical polymerization in the presence of 0.01 to 10% by weight of initiators, from monomers of cyclic sterically hindered amines of general formula (B)

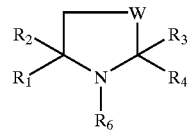

where $R_1$ to $R_4$ are: alkyl $C_1$–$C_4$, —$(CH_2)_n$— and n=3, 4, 5, $R_6$ is alkyl $C_1$–$C_4$, individually or in any combination, H, OH or oxygen radical obtained by additional oxidation and W is selected from the group including —CH(X)— a —CH(X)CH$_2$— where X is:

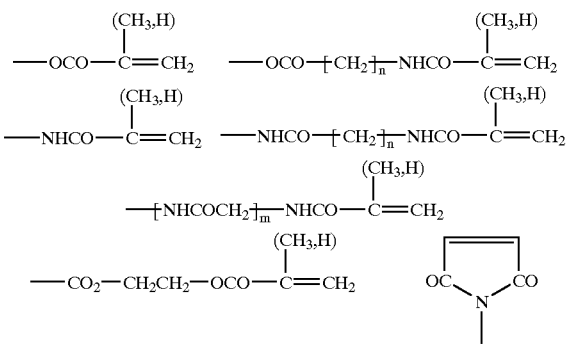

—N(X)— and —N(X)CH$_2$— where X is:

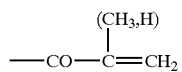

—O—, —OCH$_2$—, and $R_1$ to $R_4$ is a radical having one polymerizable vinyl group; soluble polymers prepared by polycondensation of difunctional sterically hindered amimes of the general formula (F)

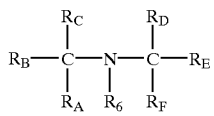

where $R_A$ to $R_F$ are: alkyl $C_1$ to $C_4$, $-(CH_2)_n-$ and n=3, 4, 5, hydroxyalkyl, aminoalkyl, carboxyalkyl (halogenide, activated ester, azide), isocyanatoalkyl in various combination and representation, $R_6$ is alkyl $C_1-C_4$, individually or in combination H, OH or oxygen radical obtained by additional oxidation;

soluble polymers or copolymers prepared by polycondensation of difunctional cyclic sterically hindered amines of the general formula ((G)

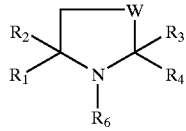

where $R_1$ to $R_4$ are: alkyl $C_1-C_4$, $-(CH_2)_n-$ and n=3, 4, 5, hydroxyalkyl, aminoalkyl, carboxyalkyl (halogenide, activated ester, azide), isocyanatoalkyl, $R_6$ is alkyl $C_1-C_4$, individually or in combination H, OH or oxygen radical obtained by additional oxidation and W is selected from the group $-O-$, $-OCH_2-$, $-NH-$, $-NHCH_2-$ where $R_1-R_4$ is hydroxyalkyl, aminoalkyl, carboxyalkyl (halogenide, activated ester, azide), isocyanatoalkyl) $-CH(X)-$, $-CH(X)CH_2-$, where X is:

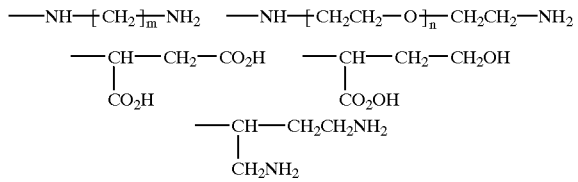

n is 1 to 10, m is 2 to 10

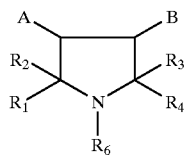

where A, B are $-OH$, $-NH_2$, $-COOH$;

soluble copolymers prepared by polycondensation of difunctional cyclic, sterically hindered amines of the general formula (G) and monofunctional cyclic sterically hindered amines in an amount of 0.1 to 15%. by weight, based on the total polymerization mixture of the general formula (H)

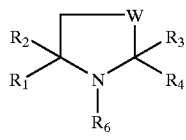

where $R_1$ to $R_4$ are: alkyl $C_1-C_4$, $-(CH_2)_n$ and n=4 or 5, hydroxyalkyl, aminoalkyl, carbokyalkyl, ore their reactive derivatives, $R_6$ is alkyl $C_1-C_4$, individually or in combination H, OH or oxygen radical obtained by additional oxidation and W is selected from the group consisting of: $-O-$, $-OCH_2-$, $-NH-$, $-NHCH_2-$, where $R_1$ to $R_4$ is hydroxyalkyl, aminoalkyl, carboxyalkyl, CH(X)— a CH(X) CH$_2-$ where X: $-COOH$ (halogenide, activated ester, mixed anhydride, azide), $-NCO$,

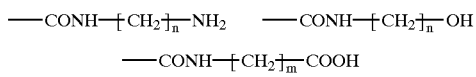

where n is 2–10, m is 1–10;

derivatives of sterically hindered cyclic amines of general formula

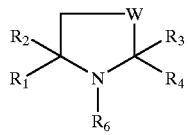

where $R_1$ to $R_4$ are: alkyl $C_1-C_4$, $-(CH_2)_n-$ and n=3 to 5, hydroxyalkyl, aminoalkyl, carboxyalkyl, in combination and any representation $R_6$ is alkyl $C_1$ to $C_4$, H, OH or oxygen radical in any representation and W is represented by following groups: $-O-$, $-OCH_2-$, $-NH-$, $-NHCH_2-$, $-CH(X)-$. $-CH(X)CH_2-$, where X=

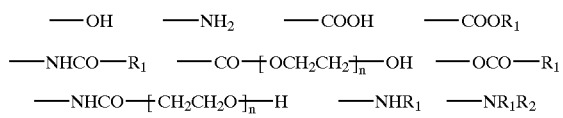

and $R_1$, $R_2$ are alkyl $C_1-C_{10}$;

polymers, copolymers, natural compounds comprising free reactive groups $-OH$, $-NH_2$, $-COOH$, $-CHO$, oxiran, selected from the group consisting of poly(vinyl alcohol), cellulose, (2-hydroxyethyl)cellulose, (carboxymethyl) cellullose, agar derivatives, polymers obtained by condensation, using dihydroxyalkane derivatives, oligomers and polymers of ethylene glycol or propylene glycol, natural o synthetic polymers, comprising a free carboxyl group, amino group or aldehyde group, prepared by additional functionalization of polymers or natural compounds by polymer-analogous reaction with a suitable sterically hindered amine selected from the group comprising:

4-X-1-$R_6$-2,2,6,6-tetramethyl-piperidine

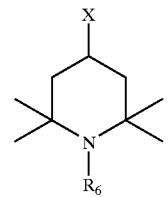

where X is $-NH_{2,i}$ $-OH$, -halogen, $-NCO$, $-COOH$ (halogenide, activated ester, mixed anhydride, azide), $-CH_2Br$ and $R_6$ is alkyl $C_1-C_4$, individually or in combination, H, OH or oxygen radical obtained by additional oxidation;

(n-X-alkyl)-1-$R_6$-(2,2,6,6-tetramethyl-piperidin-4-yl)amine of the general formula

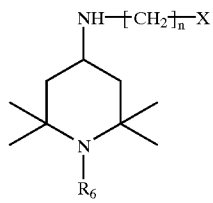

where n=1 to 10, X is halogen, —OH, —NH$_2$, —COOH, (halogenide, mixed anhydride, activated ester, azide), R$_6$ is alkyl C$_1$–C$_4$, individually or in combination, H, OH or oxygen radical obtained by additional oxidation, 1-R$_6$-(2,2,6,6-tetramethylpiperidin-4-yl)-(n+1)-X-alkanoate of general formula

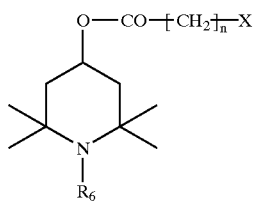

where n=1–10, X is —OH, —NCO, —COOH (halogenide, activated ester, mixed anhydride, azide), —NCO, R$_6$ is alkyl C$_1$–C$_4$, individually or in combination, H, OH or oxygen radical obtained by additional oxidation;

4-(n-X-alkyl)-1-R$_6$-2,2,6,6-tetramethylpiperidine of the general formula:

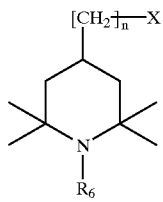

where n=1–10, X is —NH$_2$, -halogen, —OH, —NCO, —COOH (halogenide, activated ester, mixed anhydride, azide), R$_6$ is alkyl C$_1$–C$_4$, individually or in combination, H, OH or oxygen radical obtained by additional oxidation;

3-X-1-R$_6$-2,2,5,5-tetramethylpyrrolidine of general formula:

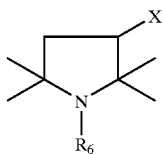

where X is —NH$_2$, —OH, —NCO, —COOH, (halogenide, activated ester, mixed anhydride, azide), —CH$_2$Br, R$_6$ is alkyl C$_1$ to C$_4$, individually or in combination, H, OH or oxygen radical obtained by additional oxidation;

1-R$_6$-(2,2,5,5 4tetramethyl-pyrrolidin-3-yl)(n+1)-X-alkanoate of the general formula:

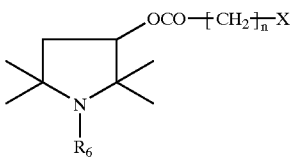

where n is 1 to 10, X is —NH$_2$, —OH, —NCO, —COOH (halogenide, activated ester, mixed anhydride, azide), R$_6$ is alkyl C$_1$–C$_4$, individually or in combination, H, OH or oxygen radical obtained by additional oxidation;

1-R$_6$-2,2,5,5-tetramethyl-2,5-dihydropyrrole-3-carboxylic acid

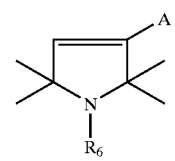

where A is —COOH, (chloride, mixed anhydride, activated ester, azide), glycidyl ester, R$_6$ is alkyl C$_1$–C$_4$, individually or in combination, H, OH or oxygen radical obtained by additional oxidation.

Further developments and improvements of the invention are demonstrated by reference to various compounds which are subject to dependent claims and the preparation and effects of which are demonstrated in the accompanying examples. The invention is based on a new finding that amines with sterically hindered amino groups are able to substantially liquidate reactive oxygen derivatives and thus to enable accelerated healing of damaged tissues. The mechanism of their effect on the living organism has not been described, however, the chemism of the elimination of the oxygen reactive radicals may be similar to that described for the polymeric systems. The presence of any of the oxidation states of such amines (hydroxylamine or nitroxide) accelerates the healing of damaged tissues since, due to the recombination with free radicals or oxidation agents, such as hydrogen peroxide, organic peroxy radicals, hyperoxides, etc. formed in the living tissue, a considerably larger spectrum of compounds for their liquidation is available.

The compounds contained in the preparation according to the invention include soluble or crosslinked polymers, which are formed from polymerizable sterically hindered amines or copolymers, wherein, besides a sequence formed from a polymerizable amine, any suitable monomer may be incorporated, advantageously a hydrophilic one. The accessibility of the amino group is from the steric point of view substantially restricted. The stabile free radicals derived from that group of compounds are not able to initiate a radical polymerization. The sterically hindered amines may survive the polymerization in their original form or, i.e., as amine or, as the case may be, in a higher oxidation state i.e. as hydroxylamine or nitroxide.

This type of amines or their derivatives preferably react with oxygen and its reduced derivatives such as superoxide, hydroxyl radical, hydrogen peroxide, alkyl peroxides, alkyl hyperoxides, etc. and protect the tissue from destructive oxidation. The hydrophilic polymers are suitable for applications in medicine in the form of gels, foils, therapeutic- .contact lenses, powders, etc. In a proper configuration such as foam, sponge, etc. The aforesaid polymeric systems may simultaneously remove water from the injured tissues.

The same effect results in production of polymers prepared by condensation of di- or polyfunctional alcohol, amines, aminoalcohol with reactive derivatives of di- and polyfunctional acid derivatives such as chlorides, activated esters, mixed anhydrides, or bifunctional isocyanates, upon formation of polyesters, polyamides, urethanes or their combination compounds. In such polymers formed by condensation, it is of course assumed that they contain a built-in sterically hindered amine provided with suitable reactive groups. Such polymers prepared by condensation may be prepared, dependent on the polymerization condition, in a soluble or crosslinked form.

In connection with the new preparation, the antibacterial effect of quaternary ammonium salts may be used and in this case the therapeutic effect of the polymeric derivatives of the sterically hindered amines and their oxidation derivatives may be combined with the therapeutic effect of the polymeric derivatives of quaternary ammonium salts in order to achieve substantially prolonged period, which may be necessary for the application of polymeric systems, without causing a contamination. The enhanced antibacterial effect, for example with a denture prosthesis may be secured by the presence of bonded quaternary ammonium salts which may be prepared by copolymerization of the above specified polymerization mixtures with the polymerizable quaternary salts or precursors thereof and their subsequent quaternization or by condensation of substituted amines in such a manner that the quaternization may be carried out subsequently.

The method of preparation of copolymers consists in the polymerization of a polymerization mixture including some of the above described vinyl monomers or a combination thereof, a polymerizable sterically hindered amine or a mixture thereof or, as the case may be, a hydroxylamine derivative and, if necessary, a crosslinking agent and initiator under formation of a soluble or insoluble polymer powder or a required article formed in the polymerization mold such as foil, lens, etc. In preparation of hydrophilic gel articles, the process may be managed in such a way that in the first stage powdered hydrophilic polymers with a sterically hindered amine and amino group in various oxidation state represented by amine, hydroxylamine, or nitroxide radical or various types of derivatives of sterically hindered secondary amines in the form of powdered polymers having various oxidation state which may be combined, are prepared whereas in the second stage, the desired gel is prepared from such mixtures.

The advantage of the gel copolymer structures is that the gel may perfectly cover the lesion to be cured. Various promoting medicament forms may also be added to such gels prepared by the above process.

The polymers prepared by polycondensation are polyesters, polyamides, polyurethanes, or their mixtures. The polycondensation is carried out either with a bifunctional sterically hindered secondary amine or in the presence of other bifunctional monomers. The preparation of such polymers is governed by common rules of preparation of polymers by polycondensation.

In both soluble and insoluble polymers formed by condensation, quaternary ammonium salts may be incorporated therein by means of suitable derivatives. The precursors must be additionally quaternized.

BRIEF DESCRIPTION OF DRAWING

The FIG. 1 of the drawing shows an EPR spectrum of an immobilized nitroxide radical in a contact lens after oxidation with hydrogen peroxide according to Example 16.

EXAMPLES

Example 1

Figure 1:
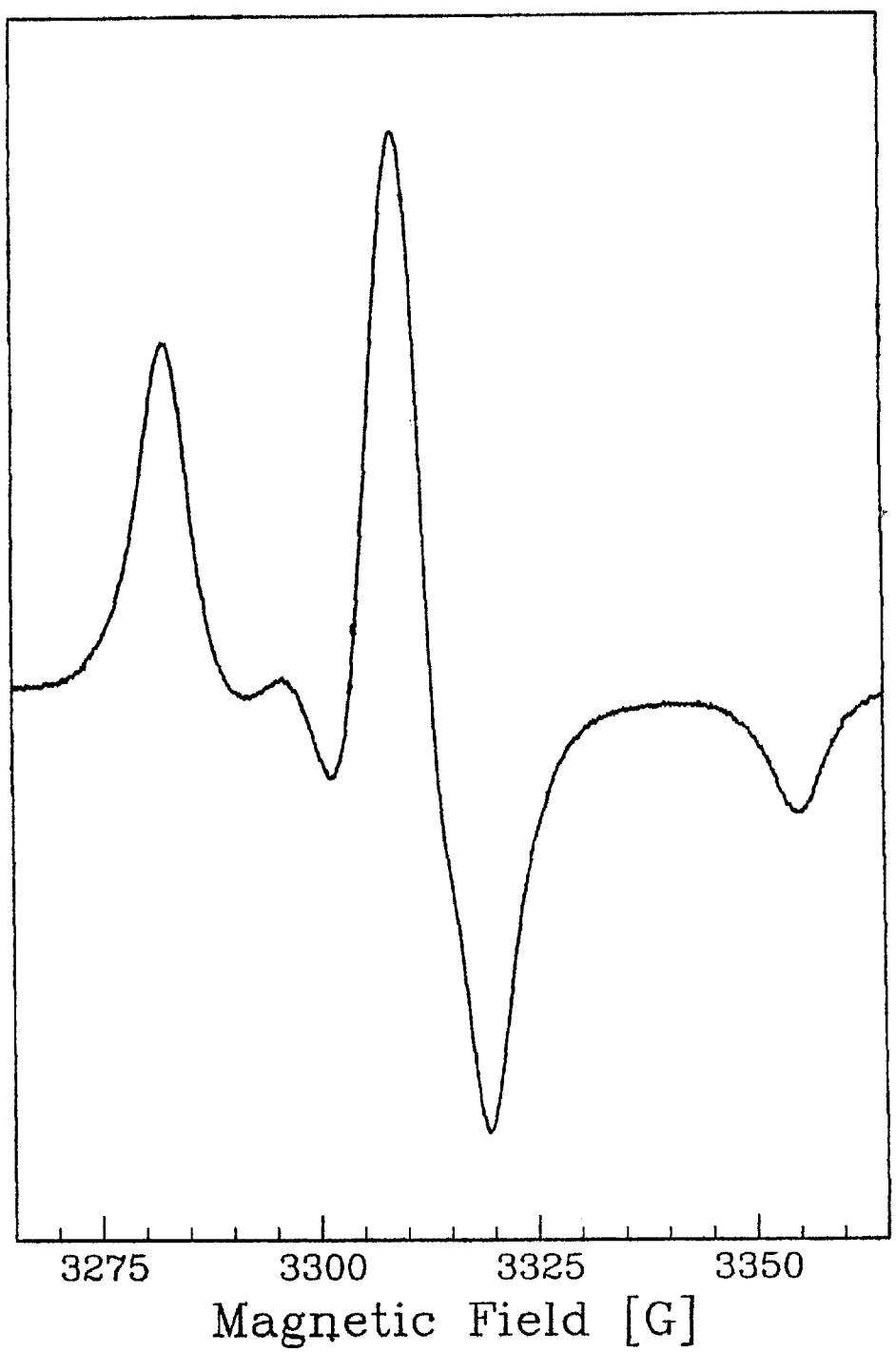

A mixture of 80 g 2-hydroxyethyl methacrylate, 0.5 g N-(2,2,6,6-tetramethyl-piperdin-4-yl)methacrylamide, 0.6 g ethylene glycol dimethacrylate, 0.5 g 2,2'-azobis(2-methyl-propanenitrile) (AIBN) was heated in 1000 ml benzene at 70° C. for a period of 12 hours. The formed polymer was extracted at room temperature with 1000 ml of benzene. The powdered polymer was agitated in a mixture water—poly (ethylene glycol) 300 (macrogolum 300), to obtain a gel of required consistency suitable for therapeutic applications.

Example 2

A polymerization mixture prepared in accordance with Example 1 and after adding 0.08 g 2-dimethylaminoethyl methacrylate was polymerized in 1000 ml benzene at a temperature of 70° C. for a period of 12 hours. The copolymer has been extracted with 1000 ml benzene and reacted with 10 ml of methyl iodide for 48 hours at room temperature and for another 2 days with 1000 ml benzene only. The obtained powdered polymer was dried.

Example 3

The polymer prepared according to Example 1 was mixed with an aqueous 4% solution of copolymer poly[(2-hydroxyethyl methacrylate)-co-2-(methacryloyloxy)ethyl-trimethylammonium bromide] solution so that the concentration of the ammonium salt in the obtained polymer amounted $10^{-5}$ g/kg.

Example 4

70 g 1-vinylpyrrolidin-2-one, 10 g 2-methoxyethyl methacrylate, 7 g N-(2,2,6,6-tetramethyl-piperidin-4-yl) acrylamide, 0.5 g 1,1'-divinyl-3,3'-(ethane-1,1-diyl)di(2-pyrrolidone), 0.1 g AIBN was heated in 300 ml of methanol at 60° C. for 10 hours. The obtained copolymer was extracted by ethanol and after drying was pulverized. The copolymer could be swollen in water to keep up to 67% water content.

Example 5

A mixture of 60 g 2-(2-hydroxyethoxy)ethyl methacrylate, 3 g 2-(methacryloyloxy)ethyl-1-$R_6$-2,2,5,5-tetramethyl-2,5-dihydropyrrole-3-carboxylate, 0.2 g 4-vinylpyridine, 0.5 g ethylene glycol dimethacrylate, 0.5 g AIBN was heated in 950 ml toluene at 72° C. for 11 hours. The copolymer was reacted at 25° C. with a mixture of 500 ml ethanol and 500 ml benzene and 10 ml methyl iodide for 72 hours. After removal of solvents, 250 ml water and 250 ml poly(ethylene glycol) 300 (macrogolum 300) was added to the resulting polymer to produce gel.

Example 6

100 g 2-hydroxyethyl methacrylate, 0.4 g ethylene glycol dimethacrylate, 1 g 2-hydroxy-2-methyl-1-phenylpropan-1-one, 6 g 2,2,6,6-tetramethyl-piperidin-4-yl methacrylate and 0.03 g 2-dimethylaminoethyl methacrylate was allowed to polymerize on a polypropylene foil for 10 min using a number of UV lamps 175 W arranged in line from a distance of 18 cm. A thick foil of 1 mm was obtained which was reacted with a mixture of ethanol-acetone (1:1) containing 0.3% methyl iodide for 48 hours. The foil can be swollen in water to take up 36% of water.

Example 7

100 g 2-hydroxyethyl methacrylate, 0.4 g ethylene glycol dimethacrylate, 1 g 2-hydroxy-2-methyl-1-phenylpropan-1-one, 6 g N-(2,2,6,6-tetramethylpiperidin-4-yl) methacrylamide was allowed to polymerize on a polypropylene foil for 10 min using a number of UV lamps 175 W arranged in line from a distance of 18 cm. A foil of 1 mm thickness was obtained and was extracted with 30% ethanol. The foil could be swollen in water to take up 36% of water. For practical use, the foil may be swollen in 50% macrogolum 300 (see the Czech Pharmacopoeia), otherwise known as poly (ethylene glycol) of molecular weight 300 for medical purposes.

Example 8

100 g 2-hydroxyetyl methacrylate, 5 g 2-acetoxyethyl methacrylate, 1-methacryloyl-3,3,5,5-tetramethylpiperazine, 0.5 g ethylene glycol dimethacrylate, 0.02 g 2-(methacryloyloxy)ethyl-trimethylammonium iodide, 0.5 g AIBN in 1000 ml toluene was heated at 72° C. for 11 hours. After extraction with benzene and drying, the copolymer was swollen by mixing thereof with 500 ml mixture water -poly(ethylene glycol) of molecular weight 400 (1:1) to obtain gel.

Example 9

100 g 2-hydroxyethyl methacrylate, 0.4 g ethylene glycol dimethacrylate, 1 g 2-methoxy-1,2-diphenylethanone, 6 g 2,2,6,6-tetramethylpiperidin-4-yl acrylate, was permitted to polymerize on a polypropylene foil for 10 min using a number of UV lamps 175 W arranged in line at a distance of 18 cm. The obtained foil, 1 mm thick, was extracted with a mixture of ethanol—acetone (1:1). The foil was oxidized with 30% hydrogen peroxide (500 ml) so that it contained 37% of nitroxide radicals (based on the amount of added polymerizable secondary amine). The foil can be swollen in water to take up to 36% of water.

Example 10

A mixture of 80 g 2-hydroxyethyl methacrylate, 5 g N-{3-oxo-3-[(2,2,6,6-tetramethylpiperidin-4-yl)amino] propyl}methacrylamide, 0.6 g ethylene glycol dimethacrylate, 0.5 g 2,2'-azobis(2-methyl-propanenitrile) was heated in 1000 ml of benzene at 70° C. for 12 hours. The obtained polymer was extracted at room temperature with 1000 ml benzene and oxidized in a suspension (1000 ml benzene) by 8 g 3-chloroperbenzoic acid for 24 hours at room temperature under continuous stirring. After drying and swelling in water, the polymer contained about 35% of water. (The content of nitroxides was 48% based on the content of the amine susceptible to oxidation).

Example 11

A mixture of 80 g 2-hydroxyethyl methacrylate, 5 g N-(2,2,6,6-tetramethylpiperidin-4-yl)methacrylamide, 0.6 g ethylene glycol dimethacrylate, 0.5 g 2,2'-azobis(2-methylpropanenitrile) was, after having been bubbled through by argon stream (10 min), dosed under inert atmosphere to molds suitable for preparation of contact lenses where the mixture was polymerized at 70° C. for 12 hours. The obtained cylinders (14 mm in diameter, 10 mm high) served as the material for production of therapeutic contact lenses by lathe cutting. After swelling in water, the lens contained 36% of water. It could be used directly for the eye treatment.

Example 12

A mixture of 80 g 2-hydroxyethyl methacrylate, 5 g 2-(methacryloyloxy)ethyl 2,2,5,5-tetramethyl-2,5-dihydropyrrolidine-3-carboxylate, 0.6 g ethylene glycol dimethacrylate, 0.5 g 2,2'-azobis(2-methylpropanenitrile) was, after bubbling through by argon stream, (10 min) dosed under inert atmosphere into molds suitable for preparation of contact lenses where it was polymerized at 70° C. for 12 hours. The obtained cylinders (14 mm in diameter, 10 mm of high) served as material for production of therapeutic contact lenses by lathe cutting. After swelling in water, the lenses were oxidized for various time periods with a 30% hydrogen peroxide solution (1 lens in 2 ml of the solution). After six days of oxidation at room temperature, the lenses were used for eye treatment after laser surgery with an outstanding effect.

Example 13

A mixture of 80 g 2-hydroxyethyl methacrylate, 5 g N-(2,2,5,5-tetramethylpyrrolidin-3-yl)methacrylamide, 0.6 g ethylene glycol dimethacrylate, 0.5 g 2,2'-azobis(2-methylpropanenitrile) was heated in 1000 ml benzene at 70° C. for 12 hours. The obtained polymer was extracted at room temperature with 1000 ml benzene and oxidized in suspension in 1000 ml benzene with 8 g of 3-nitroperbenzoic acid for 24 hours at room temperature under stirring. After drying and swelling in water, it contained about 35% of water (nitroxide content 39%, based on the amine susceptible to oxidation).

Example 14

100 g 2-hydroxyethyl methacrylate, 0.4 g ethylene glycol dimethacrylate, 1 g 2-methoxy-1,2-diphenylethanone, 3 g 2,2,6,6-tetramethylpiperidin-4-yl methacrylate, 3 g N-(1-hydroxy-2,2,6,6-tetramethylpiperidin-4-yl)methacrylamide hydrochloride was allowed to polymerize on a polypropylene foil for 10 min using a number of UV lamp 175 W arranged in line at a distance of 18 cm. The obtained 1-mm thick foil was extracted with a mixture of ethanol—acetone (1:1). The foil, after alkalinization with a 5% solution of sodium hydrogencarbonate (100 ml), was oxidized by 30% hydrogen peroxide (500 ml) so that it would contain 37% by weight of nitroxide radicals. The foil was swollen in water to take up 36% by weight of water.

Example 15

A mixture of 60 g diethylene glycol methacrylate, 3 g 2,2,5,5-tetramethylpyrrolidin-3-yl methacrylate, 0.5 g ethylene glycol dimethacrylate, 0.5 g 2,2'-azobis(2-methylpropanenitrile) was heated in 950 ml toluene for 11 hours. The copolymer was oxidized at 25° C. with a solution of 7 g 3-chloroperbenzoic acid in 500 ml ethanol and 500 ml benzene for 2 days. After removal of the solvents, the resulting polymer was treated by adding 150 ml water and, 150 ml poly(ethylene glycol) 300 to obtain gel structure. The content of nitroxides was 41% by weight.

Example 16

100 g 2-hydroxyethyl methacrylate, 0.4 g ethylene glycol dimethacrylate, 1 g 2-methoxy-1,2-diphenylethanone, 6 g 2,2,6,6-tetramethylpiperidin-4yl methacrylate and 0.03 g 2-dimethylaminoethyl methacrylate was polymerized on a polypropylene foil for 10 min with a number of UV lamps 175 W arranged in line at a distance of 18 cm. The obtained 1-mm thick foil was extracted with a mixture of 3000 ml ethanol-acetone (1:1) containing 100 ml of 30% hydrogen peroxide for 5 days. The foil could be swollen in water to keep up 36% by weight of water. The content of nitroxides was 15%. Its EPR spectrum is shown in FIG. 1.

Example 17

Copolymerization of the mixture of monomers according to Example 4 in a mould led to a foil (2 mm thick) which, after having been swollen in water, was used for treatment of burns. The healing of the wound covered by the foil was shortened by approximately 5 days in comparison with a wound not treated in this manner, at that, a considerable lower amount of pus was produced.

Example 18

The copolymer prepared according to Example 2, swollen in a mixture water—macrogolum 300 in a ratio of 1:1, was applied to,a pus producing wound. The healing of the wound was free of any complication.

Example 19

To a poorly accessible wound (between fingers), the gel prepared according to Example 3 was applied. This treatment resulted in accelerated healing in comparison with conventional methods, no infection being detected.

Example 19a

Fresh excoriations were covered by the foil prepared under Example 7. Most of them was finally healed in 3 days.

Example 20

Infected excoriations were treated by the foil prepared according to Example 7; the foil was replaced in the intervals of 2 days in dependence on the pus generation. The treatment was repeated depending on the epithelization stage, mostly 2–3 times.

Example 21

First-degree burns were covered by the foil described in Example 9. It proved to be sufficient if the surfaces were covered for 2 up 3 days. In crevices, the gel prepared according to Example 1 was applied once per day for 2–3 days. The wound was finally healed in several days without visible consequences.

Example 22

Second-degree burns were treated in a similar way. If the blisters were not injured the superficial skin need not have been removed. The burns were treated by foil rebandages prepared according to Example 7 or by application of the gel prepared under Example 1, depending on their accessibility. The foil could be replaced once for two days, the crevices were treated with the gel once a day. The healing process was accelerated without subsequent scars.

Example 23

Third- and fourth degree burns were covered by the foil prepared according to Example 7 for transport purposes and initial treatment.

Example 24

Minute bruises were covered by the foil prepared according to Example 9 for 2 days whereupon the lesions were found substantially healed.

Example 25

The location affected by a sting of insect was covered by the foil prepared under Example 38. After two days healed without any effects.

Example 26

To the contact skin inflammation, the foil prepared according to Example 9 was applied. The foil was replaced once a day for a period of 2 to 3 days (or longer depending on the inflammation degree). The results were similar to those described in connection with burns. The course of healing was milder.

Example 27

Seborrhoeic dermatitis and eczema were mostly treated by the gel prepared according to Example 1 for 1 hour per day. After 3 to 4 days of the treatment, the disease was practically healed.

Example 28

Crural ulcer was covered by the foil prepared under Example 7; the foil was replaced after one to two days depending on the healing degree. Sometimes, the foil had to be removed and replaced by a dry bandage for certain time. Substantial improvement was observed after 3 to 4 days of application.

Example 29

Chronic skin diseases, fistulas were covered by the foil prepared under Example 6. In blistering skin diseases, the foil was replaced after one to three days depending on relief upon evacuation.

Example 30

Ulcer affections of oesophagus—gastric and duodenal ulcer, Crohn disease, ulcerous colitis—the gel according to Example 1 was administered. Being non resorbable, the gel could be used for soothing of inflammation.

Example 31

Blistering skin diseases, after treatment with the gel prepared under Example 1 or a foil prepared according to Example 7 improved sensations accompanied by elimination of burning and pains were detected even if the origin of inflammation was not eliminated (for example with herpes simplex or zoster, psoriasis even with pustulous, exfoliate forms).

Example 32

Fresh excessive keloidal scars can be almost removed after application of the foil prepared according to Example 7 for a period of 10 days. The elimination of keloids was perceptible.

Example 33

Endarterial stents were covered by the foil prepared according to Example 7 to avoid the growth of atheromatosis material.

Example 34

Haemoperfusion cartridges filled with polymer beads, prepared from glycidyl methacrylate and 30% of glycol methacrylate as a crosslinking agent containing bonded 2,2,6,6-tetramethylpiperidin-4-amine through reaction of the glycidyl group with the amino group, were used for removal of excess free radicals present in diseases accompanied by excessive formation of free oxygen radicals.

Example 35

Contact lenses prepared according to Example 10 were used for treatment of cornea damaged by various media and influences such as alkalis, UV radiation, mechanical abrasion, burns, chronic inflammations, post surgery complications after eye laser application. The lenses were applied for 8 hours daily with substantial improvement after one week.

Example 36

A total denture prosthesis of the upper palate was covered by a paste prepared from a mixture of the powdered polymer made under Example 5 and 2-hydroxyethyl methacrylate and after covering the prosthesis surface by separation foil (cellophane), a detailed shape of the upper palate was formed. By the action of the present UV initiator, 2-hydroxy-2-methyl-1-phenylpropan-1-one (2%), after radiation with a UV lamp 125 W from a distance of 10 cm for 12 min, a hydrophilic elastic surface forms.

Example 37

30 g of a tri-block copolymer, poly(ethylene glycol)-poly (propylene glycol)-poly(ethylene glycol) (molecular weight 3000), 3.3 g bis(4-isocyanatocyklohexyl) methane, 0.5 g 4-hydroxy-2,2,6,6-tetramethylpiperideine-1-oxyl, 0.3 g poly (vinyl alcohol) and 0.8 g 1,4-diazabicyklo[2.2.2]octane were mixed and poured on a polyester foil. On heating with an infrared lamp at 40° C. for 2 hours, a desired film was formed.

Example 38

A mixture of 15 g poly(propylene oxide) (molecular weight 1500), 2.1 g hexane-1,6-diyl diisocyanate, 0.7 g 2-ethyl-2(hydroxymethyl)propane-1,3-diol, 0.5 g 3-(2-hydroxyethyl)-2,2,5,5-tetramethylpyrrolidin-1-yloxyl, 0.1 g 3-diethylaminopropylamine was poured on a hydrophobized glass and heated at 35° C. for 2 hours. A hydrophilic foil was obtained which was extracted by a mixture of 200 ml ethanol and 10 ml methyl iodide for 2 days. Extraction with 500 ml mixture ethanol—water followed.

Example 39

A hydrophilic contact lens was produced by lathe cutting of a block prepared by block polymerization of 2-hydroxyethyl methacrylate with 0.3% glycol dimethacrylate under standard polymerization conditions. Its surface was modified by the reaction of 3-isocyanato-2,2,5,5-tetramethylpyrrolidin-1-yloxyl with hydrophilic groups of the contact lens in a 1,2-dimethoxyethane solution. The present radical was then partly reduced to hydroxylamine with hydrogen under the overpressure of 100 mm water column and catalysis by a platinum net.

Example 40

A homopolymer prepared by anionic polymerization of 4-methacryloyloxy-2,2,6,6-tetramethyl(piperidin-1-yloxyl (molecular weight 2600) was dissolved in an ethanolic solution of poly(2-hydroxyethyl)methacrylate and a foil was cast from the solution. The foil was used for comparison for treatment of a burn at forearm. The therapeutic effect was substantially better in comparison with conventional methods.

Example 41

The ester prepared from poly(ethylene glycol) monoethyl ether (molecular weight 600) and 2,2,5,5-tetramethyl-2,5-dihydropyrrole-3-carboxylic acid was used as a 3% (by weight) admixture in polycondensation of a block copolymer poly(ethylene glycol)-poly(propylene glycol) (molecular weight 800) with hexan-1,6-diyl diisocyanate. The polymer was obtained as a foil, which was, after swelling in a mixture water—macrogolum 300, applied to bed-sores caused by long staying in bed. The results were substantially better than those obtained by conventional methods.

Example 42

Poly(ethylene glycol) (molecular weight 3000), with carboxylic acid end groups, was converted to diamide by the reaction with 4-amino-2,2,6,6-tetramethylpiperidine using dicyclohexylcarbodiimide. This polymer served as a 5% ingredient in the radical polymerization of 2-hydroxyethyl methacrylate in a mould to obtain a 2-mm thick foil. The foil was successfully used for treatment of crural ulcers.

Industrial Applicability

The preparation according to the invention is widely applicable for prevention and healing of inflammation diseases, surface injuries of skin, hide, fascia and muscle and lesions extending to various depths which are accompanied by a massive production of radicals by the oxygen reduction under the formation of reactive oxygen products. The preparation is applicable in sanitary, hospital and post hospital care and can be added to all preparations used as first aid means for the said types of lesion.

What is claimed is:
1. A composition for the treatment of inflammation affections, comprising:
  a soluble polymer or copolymer having at least one monomer which is a cyclic sterically hindered amine of general formula (B):

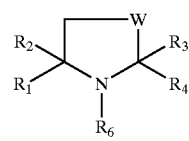

(B)

where $R_1$ to $R_4$ are: alkyl $C_1$–$C_4$, —$(CH_2)_n$— and n=3, 4, 5; $R_6$ is alkyl $C_1$–$C_4$, individually or in any combination H, OH or oxygen radical obtained by additional oxidation; and
W is —CH(X)—, and where X is:

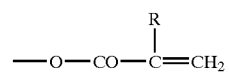

where R is $CH_3$ or H.

2. The composition of claim 1, selected from the group consisting of:

(1-$R_6$-2,2,6,6-tetramethylpiperidin-4-yl) acrylate, (1-$R_6$-2,2,6,6-tetramethylpiperidin-4-yl)methacrylate;

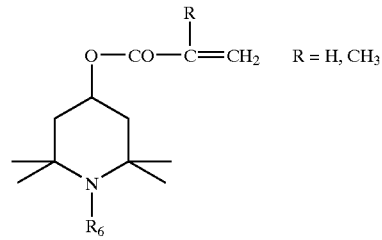

where $R_6$ is alkyl $C_1$–$C_4$, individually or in combination H, OH or oxygen radical obtained by additional oxidation;

(1-$R_6$-2,2,6,6-tetramethylpiperidine-4-yl (n+1)-(acryloylamino) alkanoate;

(1-$R_6$-2,2,6,6-teramethylpipridine-4-yl) (n+1)-(methacryloylamino)alkanoate of the general formula

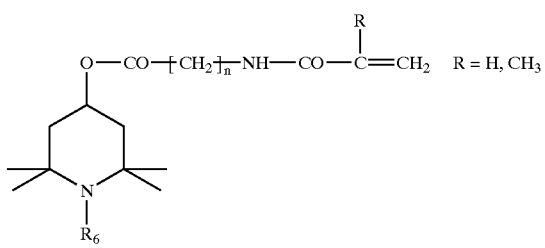

$R_6$ is alkyl $C_1$–$C_4$, individually or in combination H, OH or oxygen radical obtained by additional oxidation;

(2-acryloyloxyethyl)1-$R_6$-2,2,6,6-tetramethylpiperidine-4-carboxylate;

(2-methacryloyloxyethyl)1-$R_6$-2,2,6,6-tetramethylpiperidine-4-carboxylate;

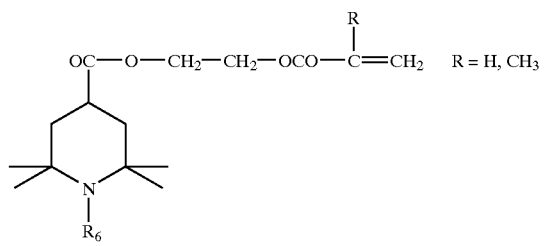

where $R_6$ is alkyl $C_1$–$C_4$, individually or in combination H, OH or oxygen radical obtained by additional oxidation;

N-(2,2,6,6-tetramethylpiperidin-4-yl)acrylamide;
N-(2,2,6,6-tetramethylpiperidin-4-yl)methacrylamide
4-acryloylamino-1-$R_6$-2,2,6,6-tetramethylpiperidine,
4-methacryloylamino-1-$R_6$-2,2,6,6-tetramethylpiperidine;

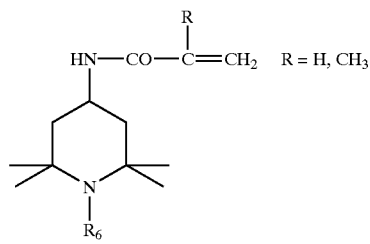

where $R_6$ is alkyl $C_1$–$C_4$, individually or in combination H, OH or oxygen radical obtained by additional oxidation;

N-(m-[(1-$R_6$-2,2,6,6-tetramethylpiperidin-4-yl) carbamoyl]alkyl) acrylamide;
N-(m-[1-$R_6$-2,2,6,6-tetramethylpiperidin-4-yl)carbonyl] alkyl) methacrylamide of the general formula:

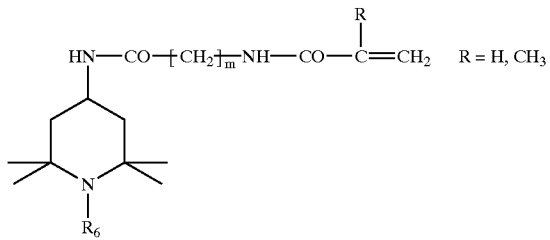

where m is 1 to 10, $R_6$ is alkyl $C_1$–$C_4$, individually or in combination H, OH or oxygen radical obtained by additional oxidation;

N-(7-$R_6$-7-azadispiro[5.1.5.3]hexadecan-15-y) acrylamide;
N-(7-$R_6$-7-azadispiro[5.1.5.3]hexadean-15-yl) methacrylamide;

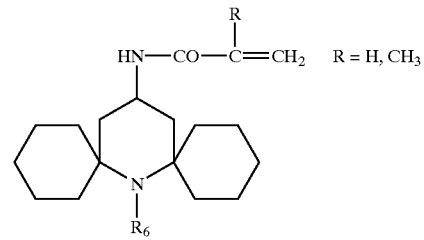

$R_6$ is alkyl $C_1$–$C_4$, individually or in combination H, OH or oxygen radical obtained by additional oxidation;

N-(1-$R_6$-2,2,5,5-tetramethylpyrrolidin-3-yl)acrylamide;
N-(1-$R_6$-2,2,5,5-tetramethylpyrrolidin-3-yl) methacrylamide;

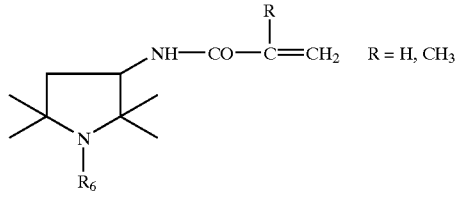

where $R_6$ is alkyl $C_1$ to $C_4$, individually or in combination H, OH or oxygen radical obtained by additional oxidation;

N-(n-[(1-$R_6$-2,2,5,5-tetramethylpyrrolidin-3-yl)carbonyl]alkyl)acrylamide;

N-(n-[(1-$R_6$-2,2,5,5-tetramethylpyrrolidin-3-l)carbonyl]alkyl)methacrylamide;

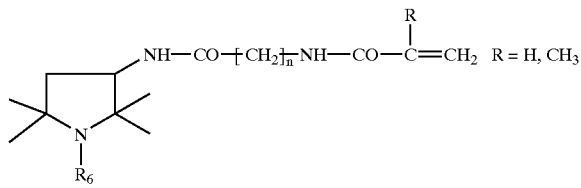

where n is 1 to 10, $R_6$ is alkyl $C_1$–$C_4$, individually or in combination H, OH or oxygen radical obtained by additional oxidation;

1-$R_6$-2,2,5,5-tetramethylpyrrolidin-3-yl acrylate, 1-$R_6$-2,2,5,5-tetramethylpyrrolidin-3-yl methacrylate;

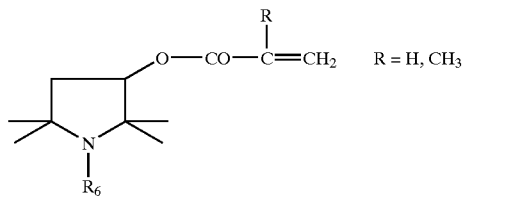

where $R_6$ is alkyl $C_1$–$C_4$, individually or in combination H, OH or oxygen radical obtained by additional oxidation;

1-$R_6$-2,2,5,5-tetramethylpyrrolidin-3-yl (n+1)(acryloylamino)alkanoate;

1-$R_6$-2,2,5,5-tetramethylpyrrolidin -3-yl (n+1)(methacryloylamino)alkanoate of the general formula

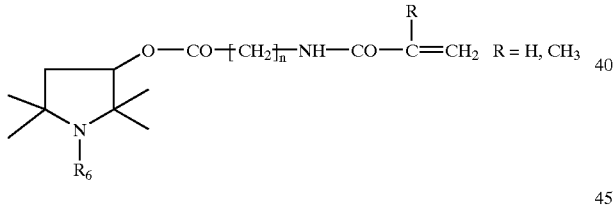

where n is 1 to 10. $R_6$ is alkyl $C_1$–$C_4$, individually or in combination H, OH or oxygen radical obtained by additional oxidation;

2-acryloyloxyethyl 1-$R_6$-2,2,5,5-tetramethyl-2,5-dihydropyrrole-3-carboxylate;

2-methacryloyloxyethyl 1-$R_6$-2,2,5,5-tetramethyl-2,5-dihydropyrrole-3-carboxylate;

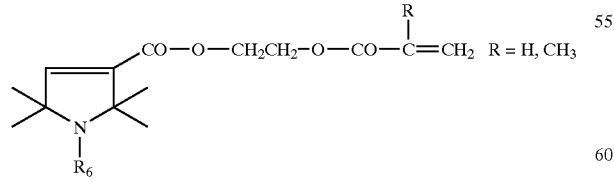

where $R_6$ is alkyl $C_1$ to $C_4$, individually or v combination H, OH or oxygen radical obtained by additional oxidation;

1-(2,2,6,6-tetramethylpiperidin-4-yl)-2,5-dihydropyrrole-2,5-dione of the general formula:

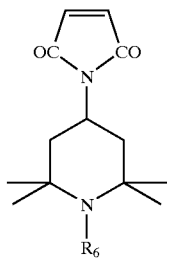

where $R_6$ is alkyl $C_1$–$C_4$, individually or in combination H, OH or oxygen radical obtained by additional oxidation;

(1-$R_6$-2,2,6,6-tetramethylpiperidin-4-yl)acrylate;

(1-$R_6$-2,2,6,6-tetramethylpiperidin-4-yl)methacrylate;

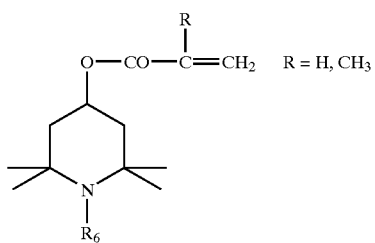

where $R_6$ is alkyl $C_1$–$C_4$, individually or in combination H, OH or oxygen radical obtained by additional oxidation;

4-$R_6$-1-acryloyl-3,3,5,5-tetramethylpiperazine;

4-$R_6$-1-methacryloyl-3,3,5,5-tetramethylpiperazine of the general formula

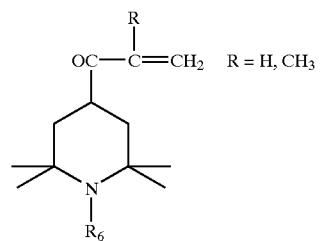

where $R_6$ is alkyl $C_1$–$C_4$, individually or in combination H, OH or oxygen radical obtained by additional oxidation;

N-(n-[(7-$R_6$-7-azadispiro[1.5.5.3]hexadecan -15-yl)carbonyl]alkyl)acrylamide;

N-(n-[(7-$R_6$-7-azadispiro[5.1.5.3]hexadecan-15-yl)carbonyl]alkyl)methacrylamide of the general formula

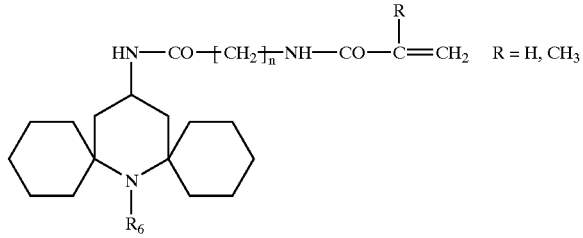

where n is 1 to 10 and $R_6$ is alkyl $C_1$–$C_4$, individually or in combination H, OH or oxygen radical obtained by additional oxidation;

N-{(n+1)-oxo-n-[(7-$R_6$-7,15-diazadispiro[5.1.5.31]hexadecane-15-yl)alkyl]}acrylamide;

N-{(n+1)-oxo-n-[(7-$R_6$-7,15-diazadispiro[5.1.5.3]hexadecane-15-yl)alkyl]}metacryl-amide of the general formula:

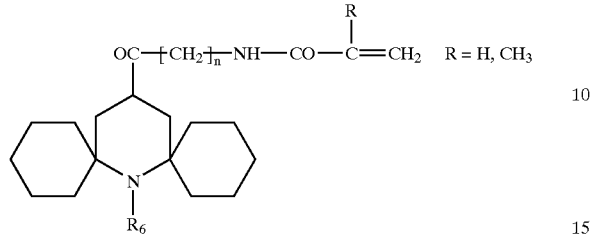

where n is 1 to 10, $R_6$ is alkyl $C_1$–$C_4$, H, OH, oxygen radical in any representation.

3. A composition for the treatment of inflammation affections, comprising:

a soluble polymer or copolymer having at least one monomer which is a cyclic sterically hindered amine of general formula (B):

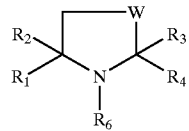

where $R_1$ to $R_4$ are: alkyl $C_1$–$C_4$, —$(CH_2)_n$— and n=3, 4, 5, $R_6$ is alkyl $C_1$–$C_4$, individually or in any combination H, OH or oxygen radical obtained by additional oxidation; and W is selected from the group including —CH(X)— and —CH(X)CH$_2$—, and where X is:

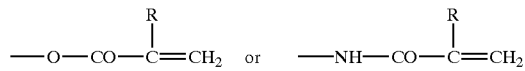

and where R is CH, or H.

* * * * *